(12) United States Patent
Lee et al.

(10) Patent No.: US 11,697,008 B2
(45) Date of Patent: Jul. 11, 2023

(54) 3D PRINTED MICRONEEDLE ASSEMBLIES

(71) Applicant: Rutgers, The State University of New Jersey, Piscataway, NJ (US)

(72) Inventors: Howon Lee, Piscataway, NJ (US); Giuseppe Barillaro, Pisa (IT); Riddish Morde, Piscataway, NJ (US); Emanuele Vignali, Massa (IT)

(73) Assignees: Rutgers, The State University of New Jersey, New Brunswick, NJ (US); Università di Pisa

(*) Notice: Subject to any disclaimer, the term of this patent is extended or adjusted under 35 U.S.C. 154(b) by 765 days.

(21) Appl. No.: 16/666,504

(22) Filed: Oct. 29, 2019

(65) Prior Publication Data

US 2020/0129748 A1 Apr. 30, 2020

Related U.S. Application Data

(60) Provisional application No. 62/751,791, filed on Oct. 29, 2018.

(51) Int. Cl.
*A61M 37/00* (2006.01)
*B29C 64/135* (2017.01)
(Continued)

(52) U.S. Cl.
CPC ....... *A61M 37/0015* (2013.01); *B29C 64/135* (2017.08); *B33Y 10/00* (2014.12);
(Continued)

(58) Field of Classification Search
None
See application file for complete search history.

(56) References Cited

U.S. PATENT DOCUMENTS

2008/0051695 A1* 2/2008 Xu ............... A61M 37/0015
604/22
2008/0269670 A1* 10/2008 Kingsford ......... A61M 37/0015
604/46

(Continued)

OTHER PUBLICATIONS

Aoyagi et al. "Biodegradable polymer needle with various tip angles and consideration on insertion mechanism of mosquito's proboscis." Sensors and Actuators A 143, (2008), pp. 20-28.

(Continued)

*Primary Examiner* — Mohammad M Ameen
(74) *Attorney, Agent, or Firm* — Lerner David LLP

(57) ABSTRACT

A microneedle assembly and a method of fabrication the assembly are provided. The microneedle assembly includes an array of microneedles attached to a base. Each of the microneedles comprise a tip, a needle shaft and a plurality of cantilevered barbs protruding outwardly from the needle shaft, where a plurality of the microneedles include two or more of the cantilevered barbs arranged in a series of concentric rings along the needle shaft of each of the plurality of microneedles. The microneedle assembly may be fabricated using a 3D printing technique, where one or more cantilevered layers are formed by exposing a photo-curable liquid resin including monomer material to a light source to create initially horizontal, cantilevered barbs having a crosslinking gradient, and rinsing to remove an amount of un-crosslinked monomers from the cantilevered layers to induce curvature in the cantilevered barbs extending towards a direction of the lower crosslinking.

27 Claims, 10 Drawing Sheets

(51) Int. Cl.
  *B33Y 10/00*      (2015.01)
  *B33Y 80/00*      (2015.01)
  *B29L 31/00*      (2006.01)
  *B29K 67/00*      (2006.01)

(52) U.S. Cl.
  CPC ...... *B33Y 80/00* (2014.12); *A61M 2037/0053* (2013.01); *B29K 2067/046* (2013.01); *B29L 2031/756* (2013.01); *B29L 2031/7544* (2013.01)

(56) References Cited

U.S. PATENT DOCUMENTS

2009/0118672 A1   5/2009   Gonnelli et al.
2013/0331792 A1   12/2013  Karp et al.
2016/0206865 A1   7/2016   Matonick et al.

OTHER PUBLICATIONS

Cho et al. "Microstructured barbs on the North American porcupine quill enable easy tissue penetration and difficult removal." PNAS, vol. 109, No. 52. Dec. 26, 2012. pp. 21289-21294.
Zhao et al. "Desolvation induced origami of photocurable polymers by digit light processing." Macomolecular Rapid Communications (2016). pp. 1-6.

\* cited by examiner

700

3D PRINTED MICRONEEDLE ASSEMBLIES

CROSS-REFERENCE TO RELATED APPLICATIONS

This application claims the benefit of the filing date of U.S. Provisional Patent Application No. 62/751,791 filed Oct. 29, 2018, the disclosure of which is hereby incorporated herein by reference.

BACKGROUND

Hypodermic needles can be used for a wide variety of medicines and are usually inexpensive. Hypodermic needles are generally made of stainless steel to assure the possibility of easy sterilization and stiffness at the same time. Typically, one end of the needle is beveled to create a sharp pointed tip letting the needle easily penetrate the skin. The other end is connected to a syringe through a connector. The syringe consists of a plunger that fits into a barrel. To collect the bio fluid or to contain the desired drug, the plunger can be pulled or pushed. Hypodermic needles are usually manufactured using a simple process known as tube drawing. Hypodermic needles are available in various sizes. The length (usually about 12-40 mm) and diameter (usually 0.25-2 mm) of the hypodermic needle can vary according to the application.

Regardless of all their benefits and advantages, hypodermic needles present a number of drawbacks and problems. For example, hypodermic needles can be invasive and/or painful. They can also can generate fear in the patient with their use. The main cause of pain is usually given by shape and dimensions: if the needle is long enough to reach the dermis and enter in contact with nerves, the piercing process can cause pain especially if the cross section is wide. Another problematic aspect with hypodermic needles is the limitation of self-administration. Administration using hypodermic needles usually requires trained healthcare personnel. This aspect not only adds to the administration cost, but it also increases patient time and cost since patients may need to travel to hospitals/clinics for injections. Still another drawback of hypodermic needles is the risk of infection and irritation of skin. Sometimes holes left by hypodermic needles are a pathway for bacteria and infections.

Microneedles (MNs) are minimally invasive devices that have been used as an alternative to traditional hypodermic needles. Due to their micro-scale structure, microneedles can overcome the skin barrier without causing significant pain to the patient. One of the main purposes for the development of microneedles was the effort to reduce the size of the needle(s) to reduce pain without affecting the volume of fluid delivered or extracted by using an array of microneedles. Typical dimensions of the microneedles are about 50-450 µm in diameter and 150-1500 µm in height. Due to their small dimensions, microneedles cause significantly less pain than hypodermic needles, as well as lower infection risks. Microneedles are also less likely to cause damage or irritation to the skin than hypodermic needles, which often cause minor bleeding at injection sites. As such, microneedles have many promising applications, including transdermal delivery of drugs, blood extraction, detection of biomarkers, skin grafting, etc.

Microneedles may be fabricated using a number of techniques. For example, microneedles may be fabricated by micro molding, where a master template may be created using a Micro-Electro-Mechanical system (MEMS), the master template may then be used to create a female mold, and finally the microneedles are created using the female mold. Creating multiple molds can be very complicated and time consuming. Another example fabrication method is drawing lithography, wherein long hollow microneedles are created using a thermosetting polymer from a 2D solid surface micropillars. However, this process can have poor reproducibility and high processing temperature, which limits the user of heat-sensitive drugs. As yet another example, 3D printing techniques can also be used to produce microneedles. For instance, microneedles may be fabricated using stereolithography (SLA), wherein polymer materials are cured layer-by-layer by exposure to light radiation, resulting in a 3D structure. However, there remains a great need to improve over existing microneedle assemblies as well as manners of manufacturing the same.

BRIEF SUMMARY

The present disclosure provides for a microneedle assembly, comprising an array of microneedles attached to a base, each of the microneedles comprising a tip and a needle shaft, and a plurality of each of the microneedles comprising a plurality of cantilevered barbs protruding outwardly from the needle shaft, wherein a plurality of the microneedles include two or more of the cantilevered barbs arranged in a series of concentric rings along the needle shaft of each of the plurality of microneedles.

At least one of the cantilevered barbs may have a downwards curvature extending downwards and away from the tip of each microneedle. At least one of the cantilevered barbs may have a length no greater than a radius of the curvature of the cantilevered barb multiplied by $\pi/2$. The concentric rings of the cantilevered barbs may be spaced apart by one or more predetermined distances along the needle shaft of each of the plurality of microneedles. At least one of the cantilevered barbs may include an upper surface that is triangular in shape. The cantilevered barbs may be formed from a polymer material that absorbs liquid such as water to cause the cantilevered barbs to change curvature during absorption of the liquid. The concentric rings of the cantilevered barbs may be substantially aligned in a series of parallel planes.

The present disclosure further provides for a three-dimensionally printed microneedle assembly comprising an array of microneedles formed by exposure of a liquid resin comprised of photopolymers to a light source layer-by-layer through a series of patterns projected onto the liquid resin, and a plurality of the microneedles comprising a needle shaft and a plurality of cantilevered barbs protruding from the needle shaft, the cantilevered barbs formed by removal of un-crosslinked monomers from one or more layers comprised of a crosslinking gradient. The crosslinking gradient may comprise a higher crosslinking at an upper portion and a lower crosslinking at a bottom portion of the one or more layers. A plurality of the microneedles may include two or more cantilevered barbs arranged in a series of concentric rings along the needle shaft.

The present disclosure further provides for providing a photocurable liquid resin including monomer material, printing an array of microneedles by exposing the polymers to a light source layer-by-layer through a series of patterns projected onto the liquid resin, the patterns being horizontal cross sections of the array of microneedles, wherein a plurality of the microneedles have a tip, a needle shaft, and a plurality of cantilevered barbs protruding from the needle shaft formed by one or more cantilevered layers, wherein, the one or more cantilevered layers are formed by exposure to the light source for a first predetermined curing time to create initially horizontal, cantilevered barbs having a crosslinking gradient with a higher crosslinking at an upper portion of the cantilevered barbs and a lower crosslinking at a bottom portion of the cantilevered barbs, and the cantilevered barbs including un-crosslinked monomers, rinsing the printed array of microneedles to remove an amount of un-crosslinked monomers from the cantilevered layers, where the removal of un-crosslinked monomers causes shrinkage of the cantilevered layers to induce curvature in the cantilevered barbs extending towards a direction of the lower crosslinking, and post-curing the rinsed array of microneedles to fix the curvature in the cantilevered barbs.

The post-curing may comprise drying the rinsed array of microneedles. The array of microneedles may further comprise a substrate forming a base for the microneedles. Each of the cantilevered barbs may be formed in a single layer. The plurality of cantilevered barbs may comprise sets of two or more barbs arranged in concentric rings around the needle shafts of a plurality of the microneedles. The curvature of the cantilevered barbs may extend away from the tip of each microneedle.

The layers of the microneedles other than the cantilevered layers may be exposed to the light source for a second predetermined curing time greater than the first predetermined curing time. The first predetermined curing time may be selected such that the curvature of the cantilevered barbs is between 0.002 $\mu m^{-1}$ and 0.007 $\mu m^{-1}$.

The liquid resin may include a photo-initiator and a photo-absorber, wherein the photo-initiator and the photo-absorber are provided in predetermined concentrations to allow a crosslinking gradient to form in the cantilevered barbs when exposed to the light source for the first predetermined curing time. The photo-initiator may comprise Phenylbis (2,4,6-trimethylbenzoyl) phosphine oxide having a concentration of between 1 and 3% w/w. The photo-initiator may comprise Phenylbis (2,4,6-trimethylbenzoyl) phosphine oxide having a concentration of 3% w/w. The photo-absorber may comprise 1-Phenylazo-2-naphthol having a concentration between 0.02 and 0.08% w/w. The photo-absorber may comprise 1-Phenylazo-2-naphthol with a concentration of 0.05% w/w. The predetermined concentration of the photo-absorber may be selected such that the curvature of the cantilevered barbs is between 0.003 $\mu m^{-1}$ and 0.004 $\mu m^{-1}$. The predetermined concentration of the photo-initiator is selected such that the curvature of the cantilevered barbs is between 0.003 $\mu m^{-1}$ and 0.004 $\mu m^{-1}$.

The present disclosure further provides for a microneedle assembly formed by providing a photocurable liquid resin including monomer material, printing an array of microneedles by exposing the polymers to a light source layer-by-layer through a series of patterns projected onto the liquid resin, the patterns being horizontal cross sections of the array of microneedles, wherein a plurality of the microneedles have a tip, a needle shaft, and a plurality of cantilevered barbs protruding from the needle shaft formed by one or more cantilevered layers, wherein, the one or more cantilevered layers are formed by exposure to the light source for a first predetermined curing time to create initially horizontal, cantilevered barbs having a crosslinking gradient with a higher crosslinking at an upper portion of the cantilevered barbs and a lower crosslinking at a bottom portion of the cantilevered barbs, and the cantilevered barbs including un-crosslinked monomers, rinsing the printed array of microneedles to remove an amount of un-crosslinked monomers from the cantilevered layers, where the removal of un-crosslinked monomers causes shrinkage of the cantilevered layers to induce curvature in the cantilevered barbs extending towards a direction of the lower crosslinking, and post-curing the rinsed array of microneedles to fix the curvature in the cantilevered barbs.

The present disclosure further provides for a microneedle assembly formed by providing a photocurable liquid resin including monomer material, printing an array of microneedles by exposing the polymers to a light source layer-by-layer through a series of patterns projected onto the liquid resin, the patterns being horizontal cross sections of the array of microneedles, wherein a plurality of the microneedles have a tip, a needle shaft, and a plurality of cantilevered barbs protruding from the needle shaft formed by one or more cantilevered layers, wherein, the one or more cantilevered layers are formed by exposure to the light source for a first predetermined curing time to create initially horizontal, cantilevered barbs having a crosslinking gradient with a higher crosslinking at an upper portion of the cantilevered barbs and a lower crosslinking at a bottom portion of the cantilevered barbs, and the cantilevered barbs including un-crosslinked monomers, rinsing the printed array of microneedles to remove an amount of un-crosslinked monomers from the cantilevered layers, where the removal of un-crosslinked monomers causes shrinkage of the cantilevered layers to induce curvature in the cantilevered barbs extending towards a direction of the lower crosslinking, and post-curing the rinsed array of microneedles to fix the curvature in the cantilevered barbs, wherein the liquid resin includes a photo-initiator and a photo-absorber, wherein the photo-initiator and the photo-absorber are provided in predetermined concentrations to allow a crosslinking gradient to form in the cantilevered barbs when exposed to the light source for the first predetermined curing time.

DETAILED DESCRIPTION

Overview

Figure 1A:
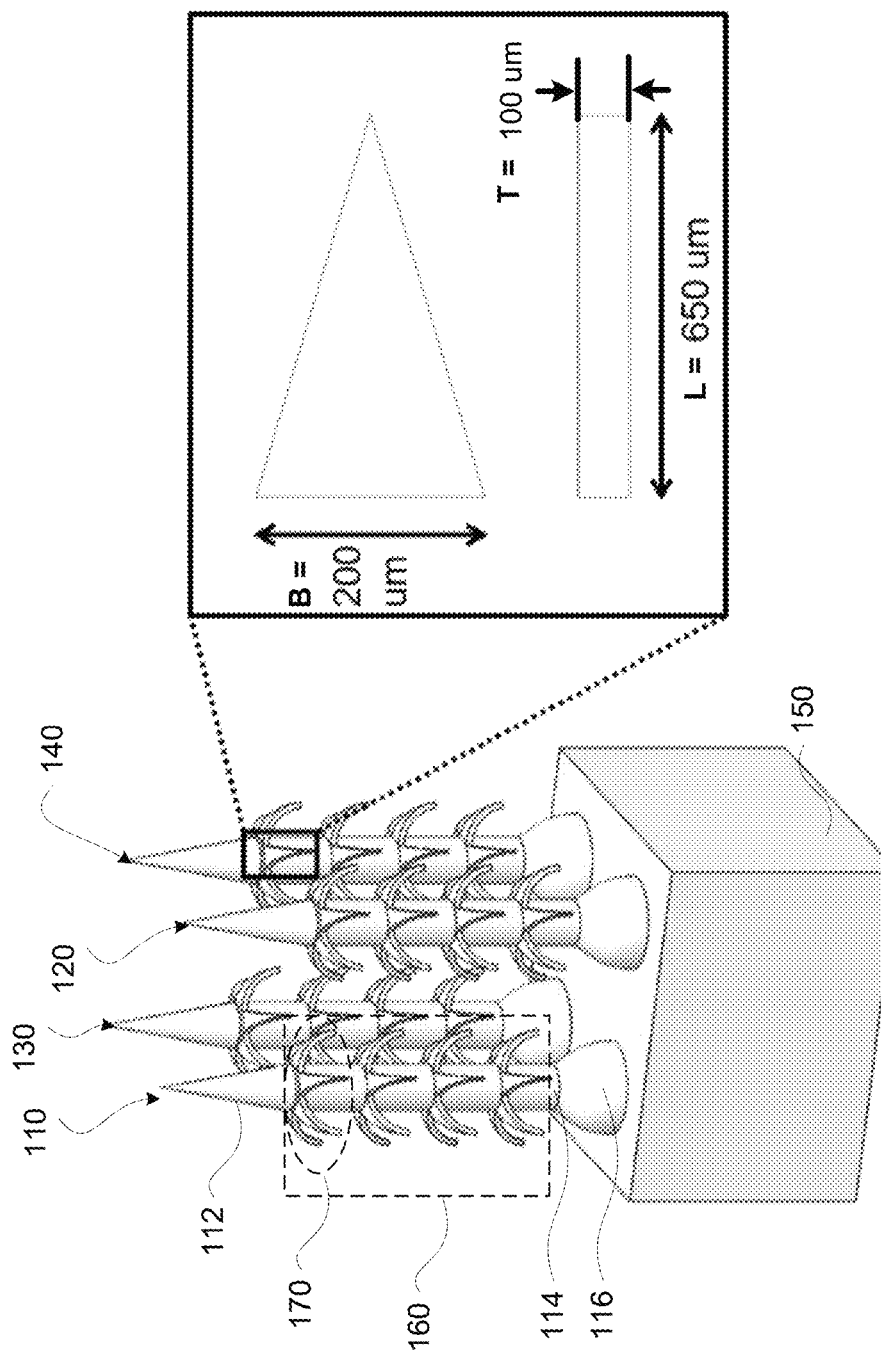
FIGS. 1A-C show various views of an example microneedle device according to aspects of the disclosure.

The technology relates generally to microneedle devices and assemblies, and fabrication methods of microneedle devices. Despite the advantages of microneedles described above, a current challenge is to achieve significant tissue adhesion over long periods of time. For instance, diabetic patients may need multiple injections throughout the day/night to ensure that a correct amount of glucose is released at the right time, and thus there is a need for microneedles that can be used multiple times and for long periods of time. In another instance, skin grafting requires microneedles with adhesive strength comparable to that of staples or sutures.

To meet these needs, aspects of the present invention provide a microneedle assembly and fabrication methods for making such microneedle assemblies. In one aspect, a microneedle assembly may be fabricated with an array of microneedles attached to a base. Each of the microneedles, or a plurality of the microneedles, may include a tip, a needle shaft and a plurality of cantilevered barbs protruding outwardly from the needle shaft. A plurality of the microneedles include two or more of the cantilevered barbs arranged in a series of concentric rings along the needle shaft of each of the plurality of microneedles. In order to improve adhesion, each or a plurality of the cantilevered barbs may have a downwards curvature extending downwards and away from the tip of each microneedle. As such, these microneedles resemble the backward-facing barbs on a porcupine quill or a honey bee stinger. When inserted into skin, these curved barbs point away from the needle tips to enable mechanical interlocking with skin tissue and thereby enhance adhesion.

Dimensions of the microneedle assembly may be adjusted to optimize adhesive strength of the microneedles. For example, curvature of the barbs may be increased to increase the adhesive strength of the microneedles. Pitch and length of the barbs may also be adjusted to maximize adhesive strength of the microneedles. Further, arrangements of the barbs, such as the number of barbs in each ring and the number of rings on each microneedle, may also be adjusted to maximize adhesive strength of the microneedles.

Aspects of the present invention use unique 3D printing techniques using crosslinking gradients to fabricate the microneedle assembly. Such improved fabrication techniques can provide faster processes to fabricate the microneedle assembly. In one aspect of assembly, a photocurable liquid resin including monomer material is provided. An array of microneedles are printed by exposing the polymers to a light source layer-by-layer through a series of patterns projected onto the liquid resin. These patterns are horizontal cross sections of the array of microneedles, wherein each or a plurality of the microneedles has a tip, a needle shaft, and a plurality of cantilevered barbs protruding from the needle shaft formed by one or more cantilevered layers. The one or more cantilevered layers are formed by exposure to the light source for a first predetermined curing time to create initially horizontal, cantilevered barbs having a crosslinking gradient with a higher crosslinking at an upper portion of the cantilevered barbs and a lower crosslinking at a bottom portion of the cantilevered barbs, and the cantilevered barbs including un-crosslinked monomers. The printed array of microneedles is then rinsed to remove an amount of un-crosslinked monomers from the cantilevered layers, where the removal of un-crosslinked monomers causes shrinkage of the cantilevered layers to induce curvature in the cantilevered barbs extending towards a direction of the lower crosslinking. The rinsed array of microneedles are cured to fix the curvature in the cantilevered barbs.

The fabrication method in accordance with aspects of the present invention provides an efficient way to produce downwards bending barbs without the need to create additional supporting structures. Further, the fabrication method allows a downwards bending barb to be created in a single layer from an initially horizontal cantilevered barb. Still further, fabrication parameters may be adjusted to maximize adhesion of the microneedles with skin. For example, by changing the composition of the liquid resin and the curing time, the crosslinking gradient in the cantilevered layers may be adjusted, which in turn changes the curvature of the barbs.

Example Devices

Figure 1B:
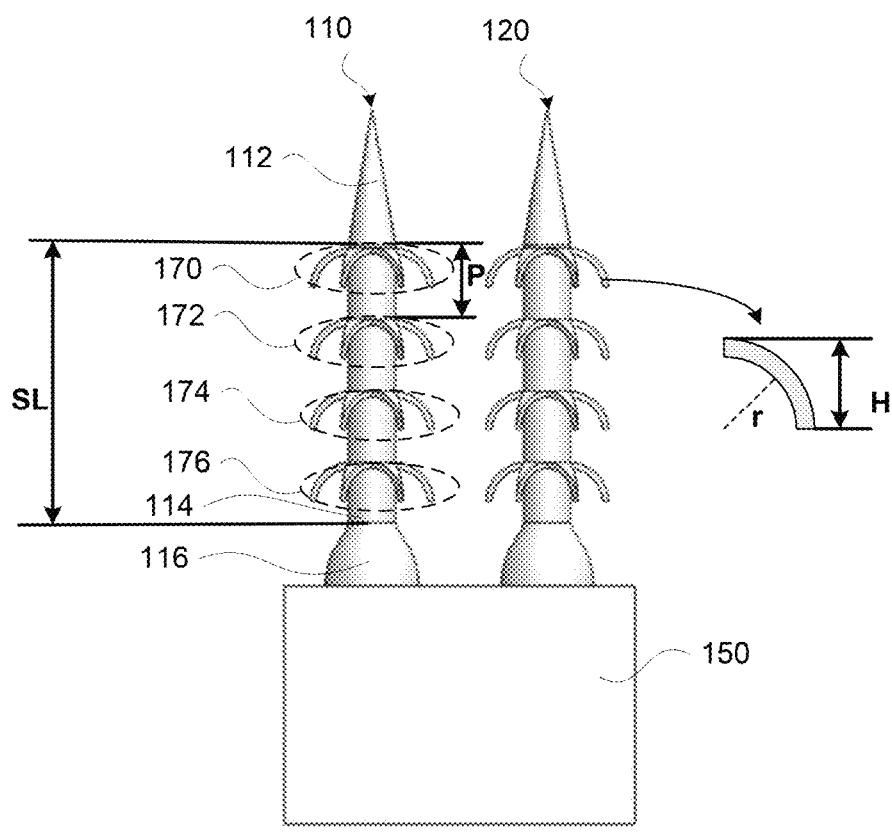
Figure 1C:
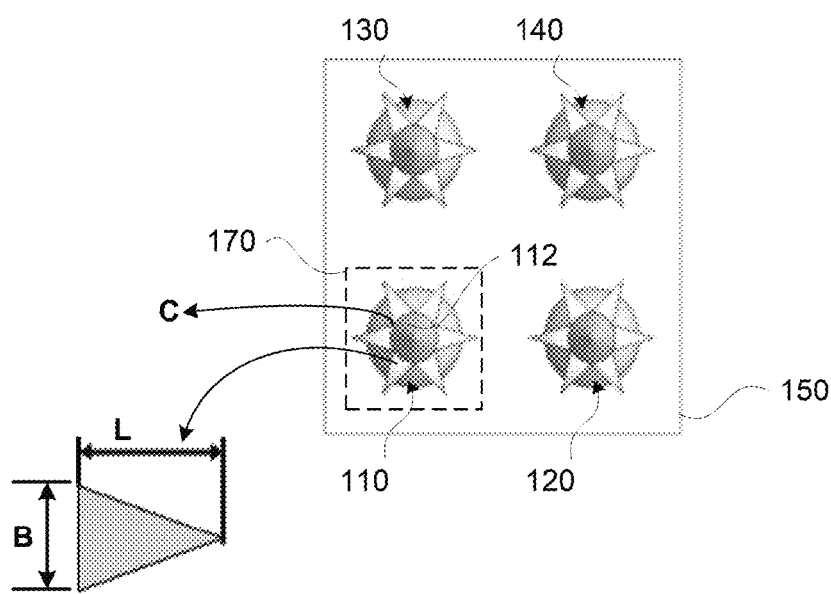

FIGS. 1A-C show various views of an example device according to aspects of the disclosure. FIG. 1A shows a perspective view of an example microneedle assembly 100. FIG. 1B shows a side view of the example microneedle assembly 100. FIG. 1C shows a top view of the example microneedle assembly 100.

Referring to FIG. 1A, the microneedle assembly 100 includes an array of microneedles, including microneedles 110, 120, 130, and 140, attached to a base 150. Although surfaces of the base 150 are shown to be rectangular in this example, the base 150 may alternatively be any other shape. Each or a plurality of the microneedles has a tip and a needle shaft. For example, microneedle 110 includes a tip 112 and a needle shaft 114. As shown, the tip 112 may have a sharp point to facilitate piercing into the skin. The needle shaft 114 may have any type of appropriate shape or a combination of shapes, such as a cylinder, a cone, a pyramid, a prism, etc. Optionally as shown, the microneedle 110 may have a base support 116 connecting the needle shaft 114 to the base 150. The base support 116 may be a conical frustum as shown, or be any other shape. The base support 116 may have a greater horizontal cross section than the needle shaft 114 in order to provide stronger attachment to base 150.

Along the needle shaft of each or a plurality of microneedle, such as needle shaft 114, a plurality of cantilevered barbs 160 protrude outwardly from the needle shaft 114. As such, after the microneedle assembly 100 are inserted into the skin, the barbs 160 may provide additional adhesive forces by interlocking with skin tissue such that the needle tip 112 and needle shaft 114 cannot easily detach from the skin. As shown more clearly in FIG. 1C, the barbs 160 may have triangular top views when viewed from the tip 112. Alternatively, the barbs 160 may have any other shape, such as a conical or pyramidal shape.

To improve adhesion with skin tissue, each or a plurality of the cantilevered barbs may have curvatures. For example as shown, each of the cantilevered barbs 160 has a downwards curvature extending downwards and away from the tip 112 of microneedle 110. As such, after the microneedle assembly 100 is inserted into skin tissue, if the microneedle assembly 100 is being pulled away from the skin, the downwards curving barbs 160 provide mechanical interlocking with the skin tissue against the direction of pulling, therefore improving skin adhesion of the microneedle assembly 100. Further, because the barbs 160 have downwards curvatures extending away from the tip 112 of microneedle 110, the barbs 160 do not significantly hinder insertion of the microneedle 110 into the skin tissue in the opposite direction.

The barbs 160 may be arranged to further increase adhesion with skin tissue. For example as shown, the barbs 160 are arranged in a series of concentric rings along the needle shaft 114 of the microneedle 110, such as ring 170. As such, each ring of barbs may engage with skin tissue independently from each other, thereby increasing overall adhesion with skin tissue. Further, as discussed below with respect to example methods, arrangement in concentric rings may facilitate layer-by-layer fabrication of the microneedle assembly. Alternatively, the barbs 160 may have other arrangements, such as distributed randomly along the needle shaft 114 or forming a spiral pattern along the needle shaft 114.

Although each microneedle of the microneedle assembly 100 is shown to have identical features and dimensions, in other examples the features and dimensions of the microneedles may vary. For example, not every microneedle needs to include the barbs, barbs on each microneedle may have the same or different arrangements, not every barb needs to have a curvature or the same curvature, etc. As shown here, concentric rings of barbs from each microneedle of the microneedle assembly 100 substantially align in a series of parallel planes. Such an arrangement may improve adhesion, as each plane consists of many barbs from multiple microneedles, as well as simplifying layer-by-layer fabrication (described below), since barbs from many microneedles may be fabricated in the same layer. However, in other examples, the rings of barbs from the various microneedles in an array may be staggered.

To provide some example dimensions, microneedle 110 in microneedle assembly 100 may have needle shafts with a length of 4000 μm and a diameter of 400 μm. The needle tip 112 may have a radius of 10 μm and a cone angle of 10°. The barbs 160 may each have a base B of 200 μm, a length L of 650 μm, and a thickness T of 100 μm. The barbs 160 may have a bending curvature of 0.0043 μm$^{-1}$, where the bending curvature is the inverse of the radius of curvature, or 1/r as shown in FIG. 1B. The microneedle 110 may have 4 consecutive rings of barbs, each ring having 6 barbs. The pitch P of the barbs may be 400 μm, which represents the distance between two consecutive rings. The microneedle assembly 100 may have an array of 2×2 microneedles. The base 150 may have a thickness of 1500 μm with a 3×3 mm$^2$ surface area. Surface area for each microneedle in the microneedle assembly 100 may be 5.5 mm$^2$ and volume for each microneedle in the microneedle assembly may be 0.47 mm$^3$.

Figure 2:
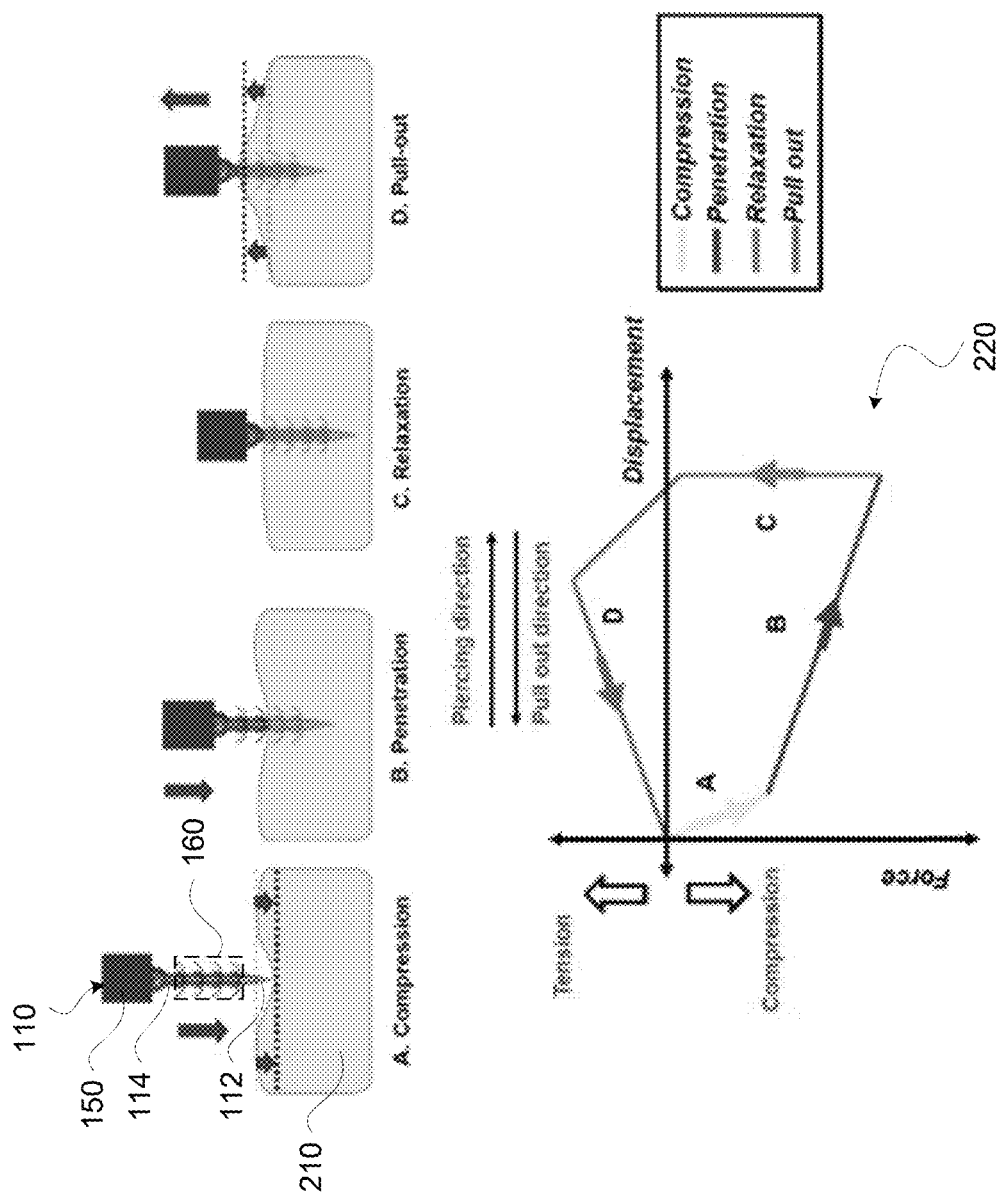
FIG. 2 is a diagram illustrating an example application of an example microneedle to an example skin tissue according to aspects of the disclosure.

FIG. 2 shows an example application 200 of the microneedle 110 of FIGS. 1A-C to an example skin tissue 210. The example application is shown in four phases A-D, along with an example plot 220 of force against displacement experienced by the microneedle during the example application.

Phase A illustrates microneedle 110 compressed against a surface of the skin tissue 210 before the skin tissue 210 is pierced through. During this phase, the surface of the skin tissue 210 is deformed and compressed against the tip 112 of the microneedle 110. As shown in the corresponding segment A of plot 220, microneedle 110 therefore experiences a displacement and a compressive load.

Phase B illustrates piercing and penetration of the skin tissue 210 by the microneedle 110. For example, once a critical compressive load is reached, the surface of the skin tissue 210 may be punctured by the tip 112 of the microneedle 110. As such, the sharpness of the tip 112 facilitates piercing of the skin tissue 210 by the microneedle 110. Afterwards, as the microneedle 110 travels deeper into the skin tissue 210, as shown in the corresponding segment B of plot 220, microneedle 110 continues to experience increased displacement and compressive load. Due to presence of the barbs 160, the compressive and friction forces experienced by the microneedle 110 are greater than if the microneedle 110 were smooth. However, because the barbs 160 curve away from the direction of piercing/penetration (indicated by arrows), these additional forces would be smaller than when the microneedle 110 is being pulled out of the skin tissue 210.

Phase C illustrates relaxation of the skin as the microneedle 110 is held still after reaching the intended depth. After the microneedle 110 stops moving deeper, the skin tissue 210 recovers over time from its deformed state, and no longer compresses against the microneedle 110. As such, the corresponding segment C of plot 220 shows that the microneedle 110 experiences no further displacement and the compressive load decrease to 0 during this phase.

Phase D illustrates the microneedle 110 being pulled from the skin tissue 210. For example, if microneedle assembly 110 is applied as a patch on a person's skin, this may occur as a result of the person's movement, or friction between the skin tissue 210 and the person's clothing, etc. During this phase, fibers of skin tissue 210 in contact with the microneedle 110, including for example the tip 112, needle shaft 114, and barbs 160, may move along with the microneedle 110. As such, the microneedle 110 experiences a tensile force due to friction from these contacts. As the barbs 160 provide additional surface area for contact with skin fibers, the barbs 160 provide additional friction forces against the skin fibers, which therefore improves adhesion of the microneedle 110 with the skin tissue 210. Further as shown, since the barbs 160 curve towards the direction of pulling (indicated by arrows), the barbs 160 provide greater friction force against the skin fibers in this direction than in the opposite direction for phase A. As such, the first portion of segment D of plot 220 shows microneedle 110 experiencing displacement and an increasing tensile force.

Eventually, when a critical amount of tensile force is applied to pull the microneedle 110, the microneedle 110 will eventually slide out of the skin tissue 210. For example, this may occur as a person tries to remove the microneedle assembly from the skin. As shown in the second portion of segment D of plot 220, when the tensile force reaches a critical point (the peak), the coefficient of friction becomes kinetic, thereafter the tensile force experienced by microneedle 110 drops as the microneedle 110 slides out of the skin tissue 210.

Thus, as illustrated by FIG. 2, the barbs 160 are structured to improve adhesion of the microneedle 110. The downwards curvature of the barbs 160 provide additional friction force by interlocking with skin tissue, and thus significantly increases the tensile force needed to pull the microneedle 110 out of the skin. Further in this regard, various parameters of the microneedle assembly 100 may be adjusted in order to maximize the adhesion of the microneedle assembly 100. In particular, the numbers, arrangements, and dimensions of the barbs on the microneedles may be adjusted to increase adhesive force with skin.

For example, with respect to the number and arrangement of barbs on the microneedles, the number of barbs in each concentric ring may be adjusted to maximize adhesion. Referring to FIG. 1C, microneedle assembly 100 is shown with six barbs arranged in each ring of barbs, such as in ring 170. In some examples, the pull-out tensile force may be increased with the number of barbs per ring, since additional barbs provide additional interlocking with skin tissue. As such, skin adhesion may be maximized by maximizing the number of barbs per ring for a given barb dimension so that the barbs do not overlap each other. For instance, given a barb base of B, and a shaft circumference of C, the maximum number of barbs per ring may be limited by C/B.

As another example to adjust the number and arrangement of barbs, a number of concentric rings of barbs may be adjusted to maximize adhesion. Referring to FIG. 1B, microneedle assembly 100 is shown with 4 concentric rings of barbs per microneedle. For example, microneedle 110 is shown with concentric rings 170, 172, 174, and 176. In some examples, the pull-out tensile force may be increased by the number of concentric rings per microneedle. For instance, because each ring of barbs independently interlocks with skin, each additional ring provide additional friction forces, which increases the overall pull-out tensile force required to remove the microneedle. As such, adhesion may be maximized by maximizing the number of concentric rings per microneedle for a given needle shaft length so that the barbs do not overlap each other. For instance, given a barb height of H, and a needle shaft length of SL, the maximum number of rings per microneedle may be limited by SL/H. In other examples, when the maximum number of rings per microneedle is used, the ring closest to the base may be too close to skin surface to provide meaningful additional pull-out force. In some cases, the ring closest to the base 150 may even cause damage to the skin surface, therefore decreasing the pull-out tensile force.

With respect to dimensions of the barbs, a number of parameters can also be adjusted to improve adhesion with skin. For example, referring to FIG. 1B, the bending curvature of the barb may be adjusted to maximize adhesion. Bending curvature of the barb can be expressed as the inverse of radius of curvature of the barb, or $1/r$. Fabrication method for maximizing bending curvature of the barbs are discussed below with respect to the example methods.

As another example, the pitch of the barb may be adjusted to maximize adhesion. Referring to FIG. 1B, microneedle assembly 100 is shown to have barbs with a pitch of P—the rings of barbs are separated by a predetermined distance of P. In some examples, the pull-out force may be increased by increasing the pitch of the barbs. For instance, as pitch increases, each ring of barbs are more likely to individually engage with skin and thus provide greater contribution to skin adhesion. However, for a fixed needle shaft length, there may be a trade-off between the number of rings and the pitch.

As yet another example, the length of the barbs may be adjusted to maximize adhesion. Referring to FIG. 1C, microneedle assembly 100 is shown to have barbs with a length of L. In some examples, the pull-out force may increase with increasing length of barbs for a given curvature up to a value, until the tip of the barb begins to bend radially inwards towards the needle shaft. As such, the pull-out force may be maximized by increasing the length of barbs up to a radius of the curvature of the cantilevered barb multiplied by $\pi/2$.

Figure 3:
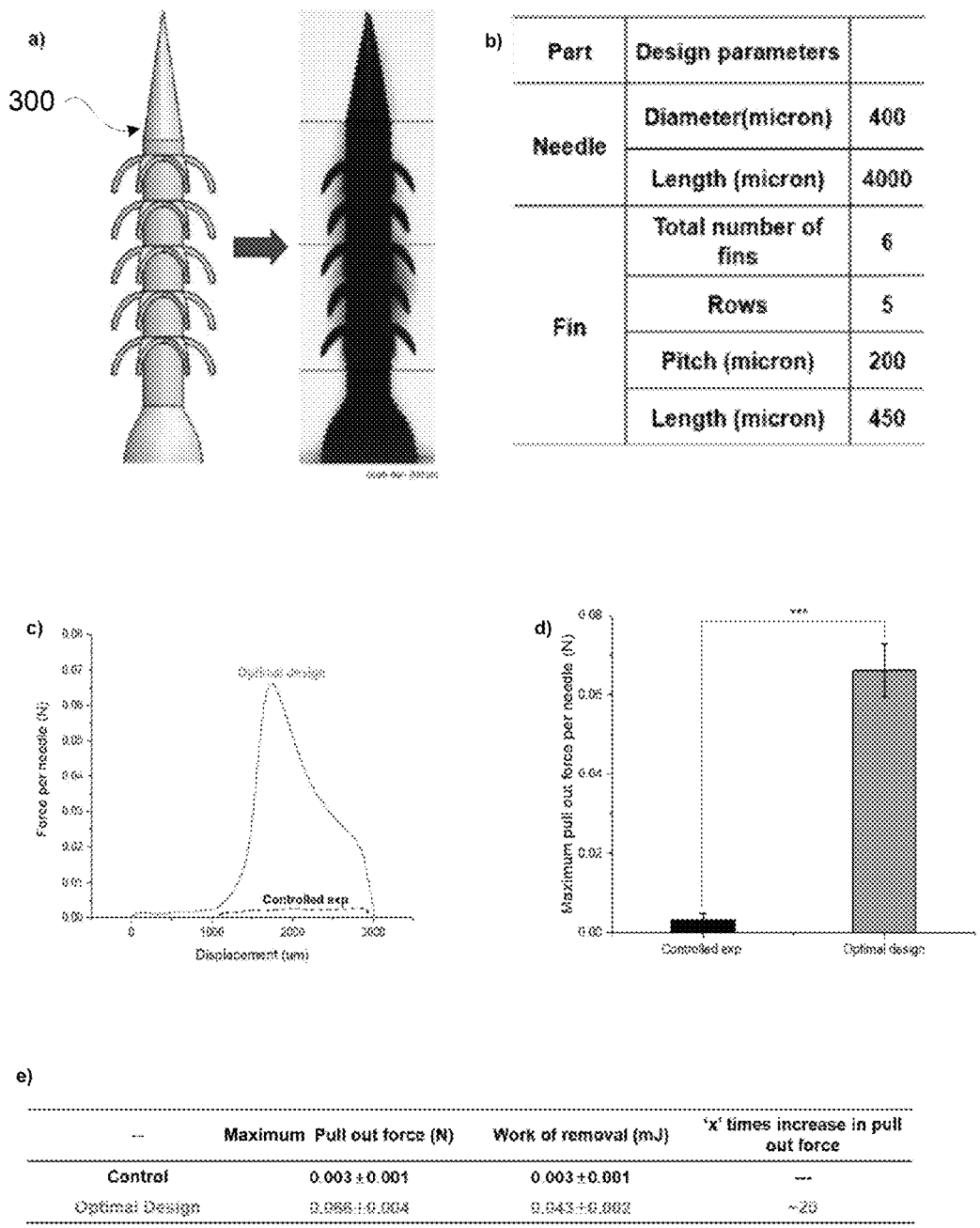
FIG. 3 shows an example microneedle (3a) with an example set of optimized parameters (3b) along with graphs (3c and 3d) and a chart (3e) of its performance statistics according to aspects of the disclosure.

FIG. 3 shows an example microneedle 300 with parameters adjusted to maximize adhesion to an example skin tissue. For example, microneedle 300 may be optimized by exploring the effects of various number, arrangement, and dimensions of barbs have on skin adhesion. Image a) shows a schematic drawing of the microneedle 300 alongside a microscopic image of the microneedle 300. Table b) provides a summary of the parameters for microneedle 300. As shown, the microneedle 300 has a diameter of 400 μm and a needle shaft length of 4000 μm. The microneedle has 6 barbs (or "fins") per ring, and 5 rings (or "rows") of barbs. The barbs have a pitch of 200 μm and a length of 450 μm.

Graph c) is a plot of force per needle against displacement for pulling microneedles out of an example skin tissue. The graph compares the tensile force experienced by the example optimal design of microneedle 300 against a control microneedle—a microneedle with same dimensions as microneedle 300 but does not have any barbs. As shown, the tensile force experienced by microneedle 300 when being pulled out of skin tissue is much greater than the tensile force experienced by the control microneedle. Therefore, the process of detaching microneedle 300 from the skin tissue is much harder than detaching the control microneedle.

Graph d) is bar graph comparing the maximum pull-out force per needle for microneedle 300 and the control microneedle. The maximum pull-out force represents the critical point where the microneedle begins to slide out of the skin tissue (peaks of graph c). As shown, the maximum pull-out force for microneedle 300 is much greater than the maximum pull-out force for the control microneedle. Therefore, it requires much greater force before microneedle 300 begins to slide out of skin tissue than for the control microneedle.

Table e) provides a summary comparison of the microneedle 300 and the control microneedle. For example, the results shown in Table e) may be averages taken from multiple experiments. As shown, the maximum pull-out force required for microneedle 300 is 0.066±0.004N, more than 20 times greater than the control microneedle, which requires a maximum pull-out force of 0.003±0.001N. The work required to pull out microneedle 300 is 0.043±0.002 mJ, more than 14 times greater than the work required to pull out control microneedle at 0.003±0.001 mJ. Thus, the presence of barbs on microneedle 300 are shown to improve skin adhesion by over 20-fold.

Referring back to FIGS. 1A-C, the microneedle assembly 100 may be made of any of a number of materials, such as polymers, ceramics, metals, etc. For example, the microneedle assembly may be made of any photocurable polymers. As a specific example, the microneedle assembly 100 may be made of a photocurable polymer material such as poly (ethylene glycol) diacrylate (PEGDA) 250. As another specific example, the microneedle assembly 100 may be made of a photocurable polymer material such as 1,6-hexanediol diacrylate. The tip 112, needle shaft 114, base support 116, barbs 160, and base 150 may be made of a same or different materials.

In drug delivery applications, the microneedles in the microneedle assembly 100 may have any of a number of structural features to allow drug to be released into skin tissue. For example, the microneedles may be coated with drug formulations prior to insertion into the skin, once inserted into the skin, the coated drug may diffuse from surfaces of the microneedles. As another example, the microneedle assembly may partially be made of dissolvable materials (for example the tips and/or needle shafts), where drug may be released during dissolution. As yet another example, the microneedles may be hollow (for example the tips and needle shafts), where drug delivery can be achieved in a similar fashion as hypodermic needles. For still another example, the microneedles may be made of a swellable material, such as hydrogel-forming matrices that may expand when fluid is absorbed from the skin tissue, thereby allowing drug molecules to diffuse out of the expanded matrices.

Figure 4:
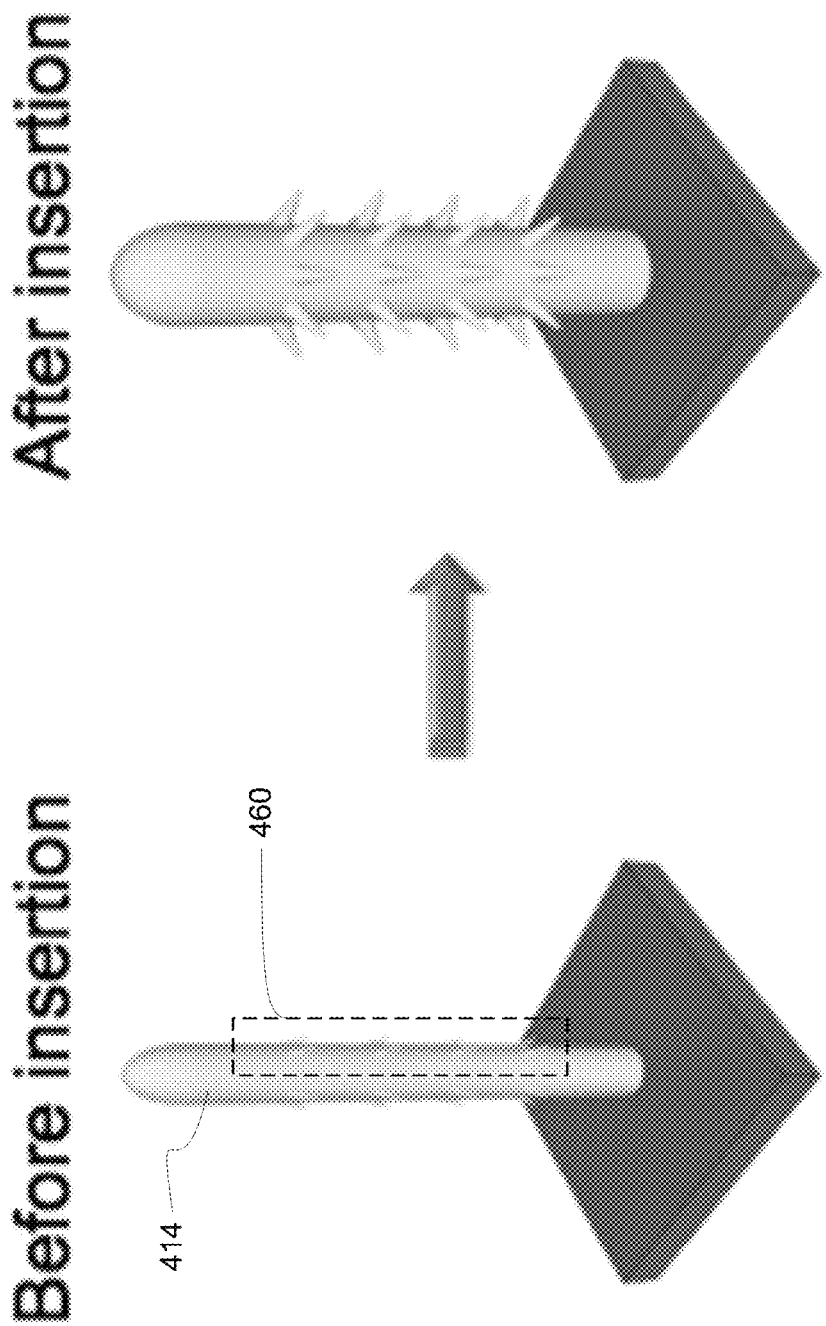
FIG. 4 shows an alternative microneedle design before and after insertion according to aspects of the disclosure.

FIG. 4 illustrates an example swellabe microneedle 400. Microneedle 400 has a plurality of barbs 460 protruding along a needle shaft 414 of the microneedle 400. Before insertion into the skin, the barbs 460 have small dimensions, therefore allowing the microneedle 400 to be easily inserted into skin tissue. Once inserted into skin tissue, microneedle 400, including the needle shaft 414 and the barbs 460 absorb fluid from skin tissue and therefore expand in size. The expanded barbs 460 provide greater interlocking with skin tissue, therefore greater tensile force are required to remove microneedle 400 from the skin. Further as shown here, due to the expansion of the barbs 460 upon absorbing fluid, the barbs 460 may "unfold"—increase their separations from the needle shaft 414—after insertion. As such, before insertion, the barbs 414, being folded closer to the needle shaft 414, may facilitate insertion into skin tissue; after insertion, the barbs 414, being unfolded farther away from the needle shaft 414, may provide greater interlocking with skin tissue to improve adhesion. In some examples (though not shown here), where the barbs have curvatures, the curved barbs may change their curvature as a result of absorbing fluid from skin tissue. The swellable microneedle 400 may be made of any of a number of swellable materials, such as polyacrylic acid.

Example Methods

Further to example systems described above, example methods are now described. Such methods may be performed using the systems described above, modifications thereof, or any of a variety of systems having different configurations. It should be understood that the operations involved in the following methods need not be performed in the precise order described. Rather, various operations may be handled in a different order of simultaneously, and operations may be added or omitted.

Figure 5:
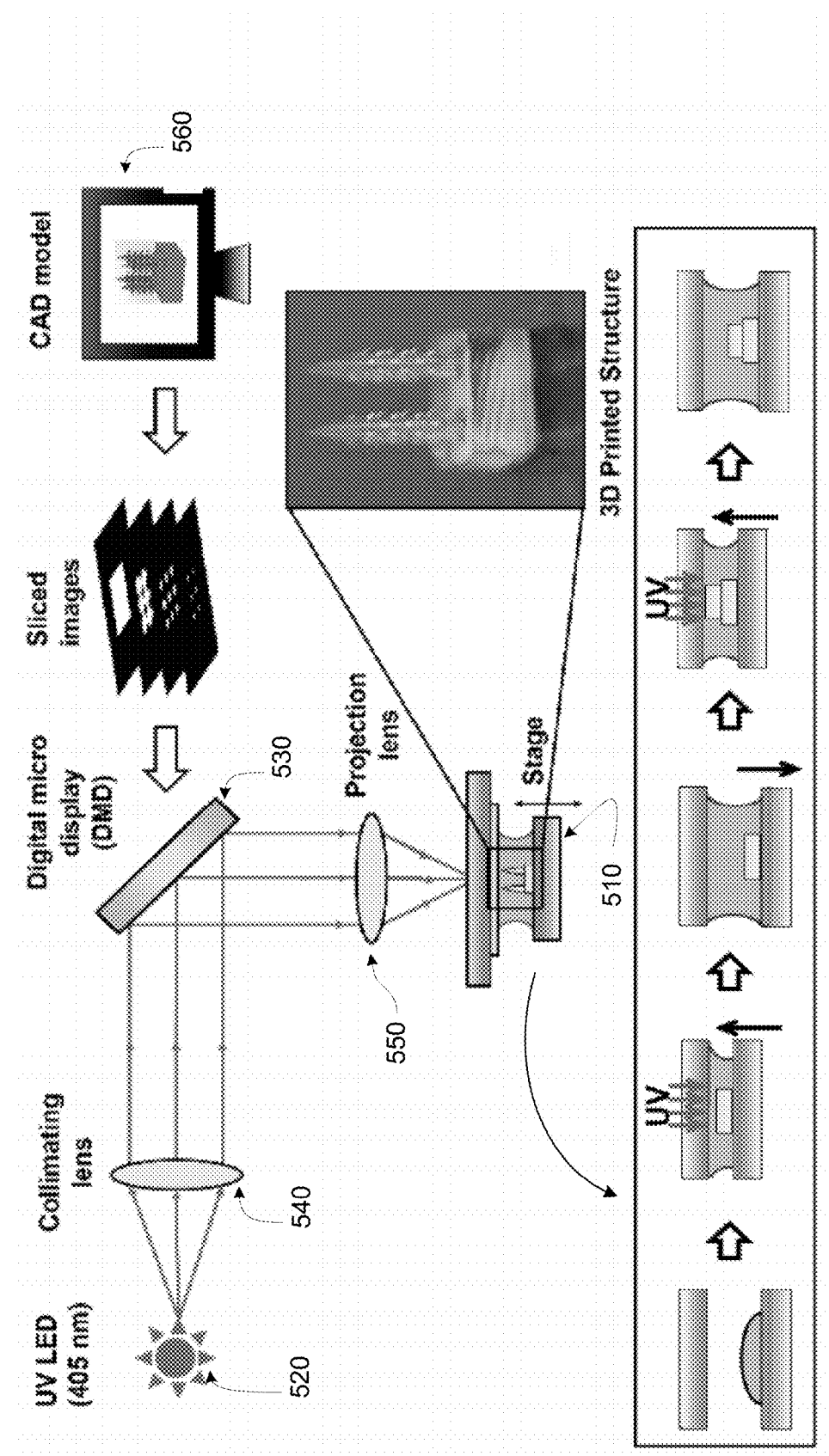
FIG. 5 is a diagram illustrating an example 3D printing system for fabrication of microneedle assemblies according to aspects of the disclosure.

FIG. 5 shows schematic drawings of an example 3D printing system 500 that can be used in the process of printing the array of microneedles, such as the microneedle assembly 100 of FIGS. 1A-C. The example system 500 can be a projection micro-stereolithography system (PuSL) including a movable stage or platform 510 on which a liquid resin including photocurable polymers may be provided for forming the microneedle array. For example, a liquid resin including polymers poly (ethylene glycol) diacrylate (PEGDA) 250 may be provided. In order to make the polymer material photocurable, the liquid resin may include additional components, such as photo-initiators and/or photo-absorbers.

A photo-initiator is a chemical that generates free radicals when exposed to radiation, such as UV or visible light radiation. As such, in accordance with aspects of the invention, a photo-initiator may be added in the liquid resin to initialize polymerization or crosslinking upon exposure to radiation. Any type of photo-initiators may be used, for example, Phenylbis (2,4,6-trimethylbenzoyl) phosphine oxide may be added to the liquid resin as a photo-initiator. As other examples, 1-[4-(2-hydroxyethoxy)-phenyl]-2-hydroxy-2-methyl-1-propane-1-one, or benzoin ethyl ether may be used as photo-initiators. The extent of polymerization may depend on a concentration of the photo-initiator present in the liquid resin. Therefore, as described below, concentration of the photo-initiator may be adjusted to achieve the desired structure. For example, 1-3% w/w of Phenylbis (2,4,6-trimethylbenzoyl) phosphine oxide may be added to the liquid resin.

A photo-absorber is a chemical that absorbs radiation, such as UV or visible light radiation, to control the radiation's penetration depth into the liquid resin. As such, in accordance with aspects of the invention, a photo-absorber may be added in the liquid resin to reduce the extent of polymerization or crosslinking with depth, thereby creating a crosslinking gradient in the layer. Any type of photo-initiators may be used, for example, 1-Phenylazo-2-naphthol may be added to the liquid resin as a photo-absorber. As other examples, quinolone yellow, hydroxyl phenyl benzotriazole derivatives (such as Tinuvin products) may be used as a photo-absorber. The gradient of crosslinking may be formed depending on a concentration of the photo-absorber present in the liquid resin. Therefore, as described below, concentration of the photo-absorber may be adjusted to achieve the desired structure. For example, 0.02-0.08% w/w of 1-Phenylazo-2-naphthol may be added to the liquid resin.

As shown, the system 500 includes a light source 520, such as a UV LED with a 405 nm wavelength. A projector 530 is included for projecting radiation from the light source 520 through a series of patterns to the stage 510 where the liquid resin may be provided. For example, the projector 530 may be a digital projector, such as a digital micro display (DMD) for projecting light patterns, such as via sliced images from a CAD model, onto the photocurable polymers. One or more collimating lenses 540 may be provided between the light source 520 and the projector 530. One or more projection lenses 550 may be provided between the projector 520 and the stage 510. In order to obtain the series of patterns, a 3D model of the array of microneedles may be designed, such as by using software 560, such as CAD software running on a computer or computer system. A series of patterns—such as horizontal cross sections of the 3D model—can then be obtained from the software program 560 and projected onto the liquid resin on stage 510 via the projector 530.

Each horizontal cross section in the series of patterns can then be used to fabricate a single layer of the microneedle array using a layer-by-layer process. An example of this layer-by-layer process is shown as a series of drawings in the box below system 500. As shown, a first layer of liquid resin is provided on the stage 510. Next, the stage 510 moves up and the first layer is exposed to radiation by the light source 520 through the first pattern of the series of patterns via the projector 530. The radiation may be provided for a predetermined curing time to induce a desired level of polymerization or crosslinking in the layer. Once structures in the first pattern are formed in the first layer of liquid resin, the stage 510 can be lowered, and a second layer of liquid resin is then provided on top of the first layer. The stage 510 then moves up, such as by a distance equal to the thickness of the first layer, so that the second layer of liquid resin can be exposed to radiation through the second pattern of the series of patterns via projector 530. Once structures in the second pattern are formed in the second layer, the stage 510 can be lowered again, and a third layer of liquid resin is provided on top of the second layer. As such, the layer-by-layer process continues until all the patterns in the series of patterns are used.

The microneedle array may be printed from bottom to top—starting from the base to the needle tips. As such, while some of the patterns in the series are used to create structures in layers that include only the base (such as base 150), base support (such as base support 116), needle shaft (such as needle shaft 114), or needle tip (such as needle tip 112) of the microneedles, other patterns in the series are additionally used to create the barbs (such as barbs 160). Fabrication of barbs curving downwards and away from the needle tips can be very challenging and the present invention addresses such problems as described herein.

For example, if the barbs curve upwards from the needle shafts towards the needle tips, layers of the barbs connected to the needle shaft could be printed first, which means subsequent layers of the barbs would be supported by the needle shaft. However, because the barbs curve downwards, printing the microneedle array from bottom to top would mean that initial layers of the barbs would be printed without support from the needle shaft. One way to solve this problem is to print the microneedle array upside-down, starting from the needle tips to the base. However, because the microneedles would be printed first without the base as support, the resulting microneedles may be distorted. Further, because the needle tips would be printed before the needle shafts, the needle tips may not be sharp. Another way to solve this problem is to use a different support material for supporting the downwards bending barbs, and wash out the support material after the microneedle array is printed. However, the support material may clog the microneedles if not washed out completely, and the washing process itself can take days, which increase fabrication time.

In order to solve these problems, a projection micro-stereolithography technique using crosslinking gradients are provided by the present invention as an efficient and improved process to fabricate the microneedle assembly. In this regard, the microneedle array is printed with cantilevered barbs that are initially horizontal. This way, layers including the horizontal cantilevered barbs can be supported by the needle shafts. However, during the printing process, a crosslinking gradient is introduced in the cantilevered barbs such that subsequent rinsing and post-curing results in the downwards curvature of the barbs.

Figure 6:
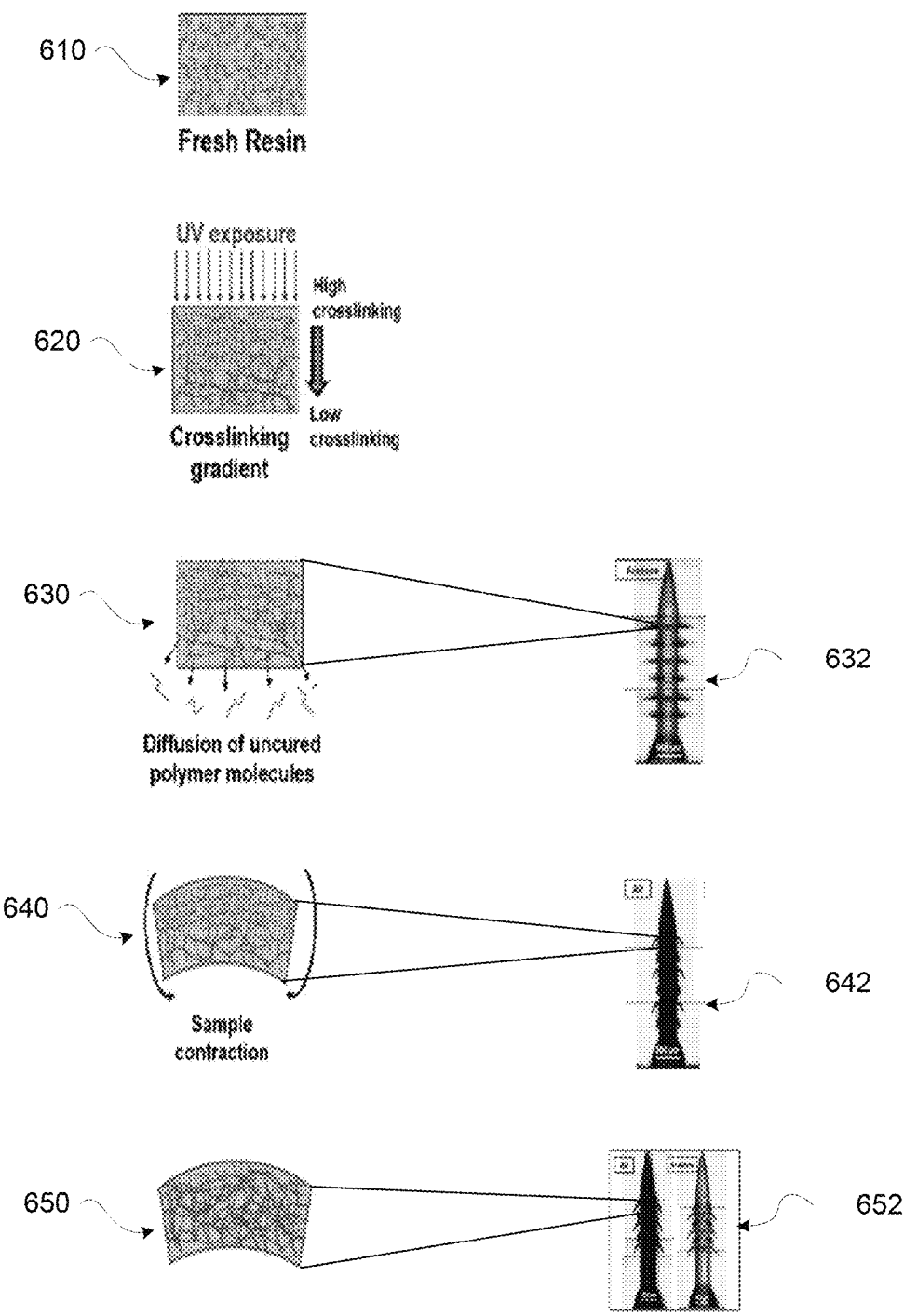
FIG. 6 is a diagram illustrating an example process of fabrication of downwards bending barbs of a microneedle assembly using crosslinking gradients according to aspects of the disclosure.

FIG. 6 illustrates an example process 600 in accordance with aspects of the present invention for fabricating the downwards bending barbs, such as downwards bending barbs 160 of microneedle assembly 100 in FIG. 1A. To illustrate the process, changes in the microscopic structure inside a layer of downwards bending barb are illustrated. For example, the example process 600 may be carried out using the example system 500 of FIG. 5.

As shown, in phase 610, a fresh layer of liquid resin is provided on stage 510 on top of a previous layer to create a layer with cantilevered barbs protruding from the needle shaft. As shown by the schematic drawing of microscopic structures within the fresh layer, the fresh layer of liquid resin contains un-crosslinked polymers indicated by short segments (as opposed to networks).

In phase 620, this fresh layer of liquid resin is exposed to radiation by the light source 520 through a pattern including horizontal barbs via projector 530. Exposure for this cantilevered layer may be for a first predetermined curing time. The first predetermined curing time may be chosen such that, at the chosen energy dosage per unit volume, a crosslinking gradient forms in the cantilevered layer, with a higher crosslinking density at an upper portion of the cantilevered barbs and a lower crosslinking density at a bottom portion of the cantilevered barbs. As shown by the schematic drawing of microscopic structures within the exposed layer, the upper portion includes mostly network-like structures, indicating a higher crosslinking density, whereas the lower portion includes fewer network-like structures, indicating a lower crosslinking density, and short segments, indicating un-crosslinked monomers.

In contrast, layers that do not include the cantilevered barbs may be exposed for a second predetermined curing time. For example, the second predetermined curing time may be chosen such that, at the chosen energy dosage per unit volume, the extent of crosslinking is substantially uniform throughout the layer. As such, the non-cantilevered layers may be exposed at a higher energy dosage per unit volume than the cantilevered layers. For example, where the cantilevered layers and the non-cantilevered layers have a same thickness, the second predetermined curing time may be longer than the first predetermined curing time. This ensures that the entire layer is highly crosslinked and a stable structure is formed for layers that do not include barbs.

In phase 630, the printed cantilevered layer with crosslinking gradient is rinsed. Although this step is shown here as the next step following printing of a cantilevered layer, this step may occur after printing of all the layers of the microneedle array. This way, only one rinse is needed for all the cantilevered layers. To rinse the cantilevered layer, organic solvents such as acetone or ethanol may be used. As shown by the schematic drawing of microscopic structures within the rinsed layer, in the bottom portion of the cantilevered layer where crosslinking is low, un-crosslinked monomers are able to diffuse out of the loose networks. However, as shown in the corresponding microscopic image 632 of the rinsed microneedle in acetone, the barbs are still horizontal at this point. This is because the structure is in a solvent, and the solvent molecules may fill the space where un-crosslinked monomers have diffused out.

In phase 640, the rinsed cantilevered layer is dried to remove the solvent from the layer. For example, the microneedle array may be dried using an air blower. Due to the loss of materials (the un-crosslinked monomers that diffused out during rinsing, as well as the solvent molecules during drying), the cantilevered layer shrinks, and bends towards the direction of lower crosslinking. As shown in the corresponding microscopic image 642 of the dried microneedle in air, at this point, the barbs bend downwards.

In phase 650, the cantilevered barb is post cured. For example, the microneedle array may be post cured in an UV oven. The post curing may be for a much longer curing time than the first and second predetermined curing times. This way, structures of the microneedle arrays become fixed (as opposed to changing shapes in different media as shown by images 632 and 642). As shown in the corresponding microscopic image 652 of the post-cured microneedle, the barbs bend downwards regardless when the microneedle is in air or in acetone.

As mentioned above with respect to the example devices, the example process 600 allows a downwards bending barb to be formed in a single layer by printing an initially horizontal cantilevered barb. As such, microneedles with downwards bending barbs can be fabricated simply by adjusting composition of the liquid resin, and setting a different curing time for the cantilevered and non-cantilevered layers. The process is therefore significantly more efficient than, for example, printing the microneedle array upside-down, or using support materials to support the barbs.

Further as mentioned above with respect to the example devices, maximizing curvature of the barbs is one way to increase adhesion of the microneedles. In this regard, a number of fabrication parameters may be adjusted to achieve better skin adhesion. The bending curvature of the barbs is highly dependent on the crosslinking gradient—the greater the crosslinking density gradient, the greater the bending curvature. Fabrication parameters that affect the crosslinking gradient can thus be adjusted, which include the curing time (the first predetermined curing time for cantilevered layers), photo-initiator concentration, and photo-absorber concentration.

Figure 7:
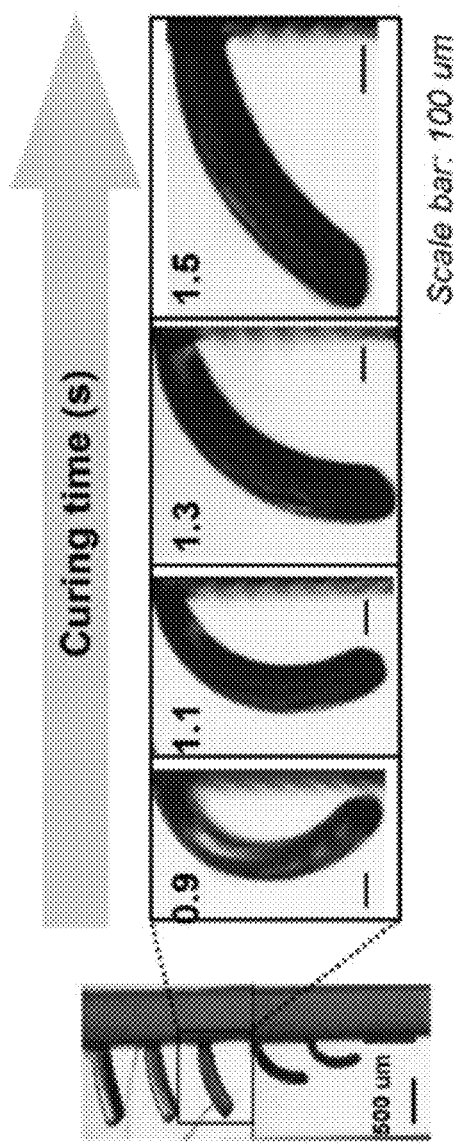
FIG. 7 is a diagram illustrating effects of curing time on curvature of the microneedle assembly barbs according to aspects of the disclosure.

FIG. 7 is a series of microscopic images 700 illustrating example effects of curing time on bending curvature of example barbs. As shown, curvature of the barb decreases with increasing curing time. This is because the longer a layer of photocurable resin is exposed to radiation, the more energy is received in the layer, resulting in greater crosslinking and therefore a thicker formed layer, including thicker barbs. As the barbs become more crosslinked and thicker, they would bend less (less shrinkage).

As shown, as curing time decreases from 1.5 s to 1.3 s, bending curvature of the barb increased. However, when curing time is decreased from 1.3 s to 1.1 s, bending curvature of the barb increased further such that the barb begins to curve inwards towards the needle shaft. These inwards bending barbs may no longer provide improved skin adhesion. An optimal curing time may then be selected such that the curvature of the barb may be maximized without the barb curving inwards towards the needle shaft, which in the example shown appears to be 1.3 s. For example, a curing time may be selected such that the curvature of the barbs is between 0.002 $\mu m^{-1}$ and 0.007 $\mu m^{-1}$.

Additionally, a threshold thickness may be required for the barbs in order to exert friction force on skin tissue. Thus, a curing time may be selected further based on a desired thickness for the barbs. For example, a curing time may be further selected such that the barbs are at least 100 µm thick.

Figure 8:
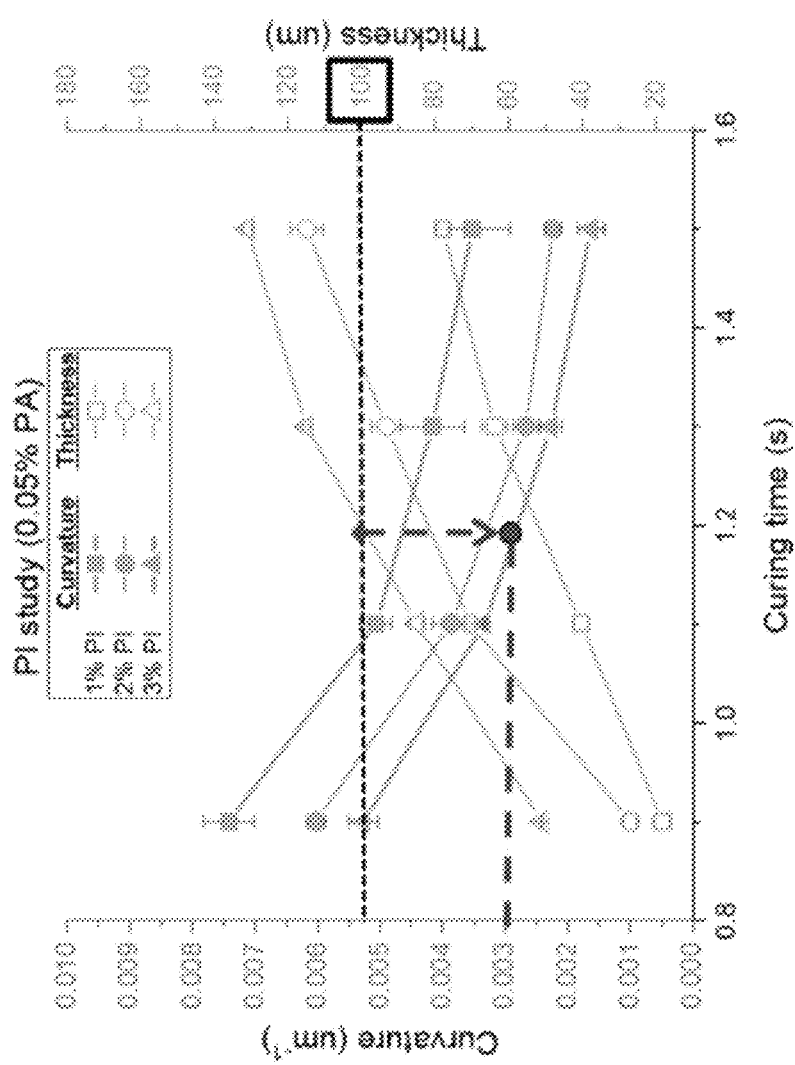
FIG. 8 is a graph showing effects of photo-initiator concentration on curvature of the barbs of a microneedle assembly according to aspects of the disclosure.

FIG. 8 is a graph 800 showing example effects of photo-initiator (PI) concentration as well as curing time on the bending curvature and thickness of the barbs. Graph 800 plots bending curvature (lines with solid points) and thickness (lines with hollow points) against curing time for 0.1% w/w, 0.2% w/w, and 0.3% w/w PI concentrations for a fixed photo-absorber (PA) concentration of 0.05% w/w. As shown, for a given curing time, bending curvature of the barb decreases with increasing PI concentration, while thickness of the barb increases with increasing PI concentration. This is because PI promotes crosslinking, thus a greater concentration of PI in the resin would decrease crosslinking gradient in the barbs, resulting in a smaller bending curvature for the barbs. Further as shown, regardless of the PI concentration, with increasing curing time, barb curvature decreases and barb thickness increases.

Based on the graph, a predetermined PI concentration may be selected such that the curvature of the barb is within a desired range, for example such as between 0.003 $\mu m^{-1}$ and 0.004 $\mu m^{-1}$. As mentioned above, since a threshold thickness may be necessary for the barbs to exert friction force against skin tissue, a PI concentration may be selected to maximize bending curvature at or above the threshold thickness. For example as shown, for 3% w/w PI, a 1.2 s curing time or greater produces barb thickness of at least 100 µm, which corresponds to a bending curvature of approximately 0.003 $\mu m^{-1}$ or lower. For another example, for 2% w/w PI, a 1.37 s curing time or greater produces barb thickness of at least 100 µm, which corresponds to a bending curvature of approximately 0.002 $\mu m^{-1}$ or lower. Thus, based on this graph, for a 0.05% w/w PA concentration, a 3% w/w PI and 1.2 s curing time may be chosen as the set of fabrication parameters that provide the greatest bending curvature and a threshold barb thickness.

Figure 9:
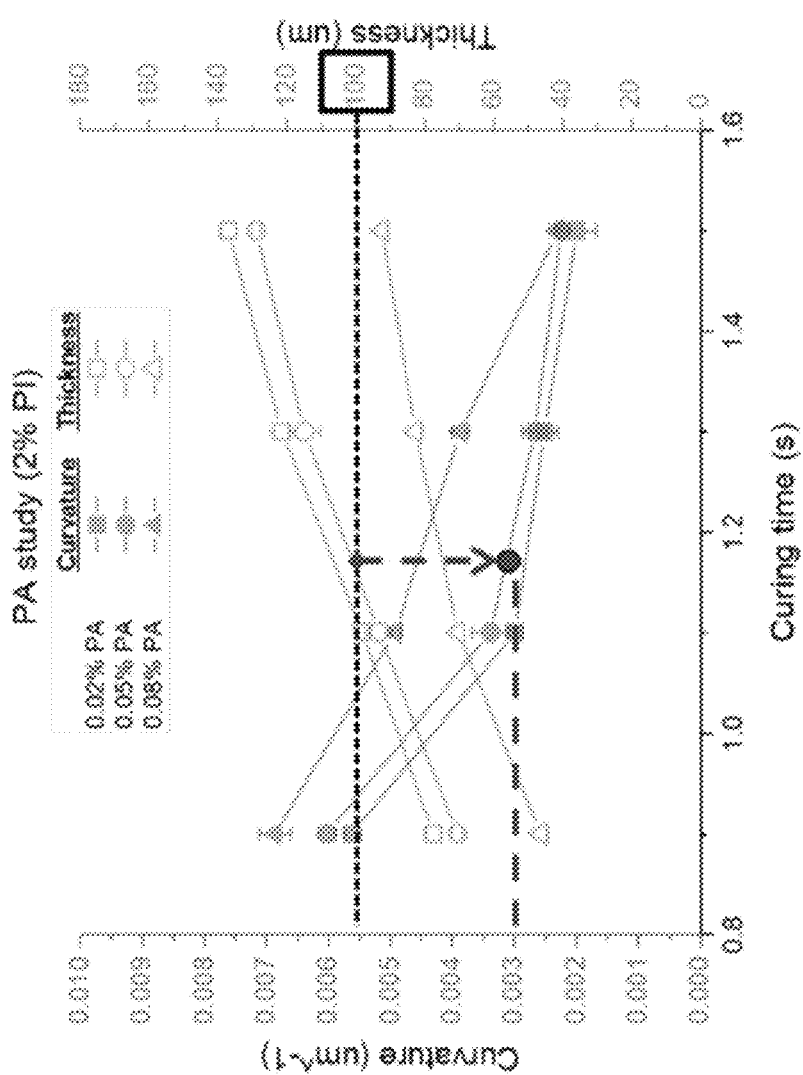
FIG. 9 is a graph showing effects of photo-absorber concentration on curvature of the barbs of a microneedle assembly according to aspects of the disclosure.

FIG. 9 is a graph 900 showing example effects of photo-absorber (PA) concentration as well as curing time on the bending curvature and thickness of the barbs. Graph 900 plots bending curvature (lines with solid points) and thickness (lines with hollow points) against curing time for 0.02% w/w, 0.05% w/w, and 0.08% w/w PA concentrations for a fixed PI concentration of 2% w/w. As shown, for a given curing time, bending curvature of the barb increases with increasing PA concentration, while thickness of the barb decreases with increasing PA concentration. This is because PA absorbs radiation and limits the radiation's penetration depth, thus a greater concentration of PA in the resin would increase crosslinking gradient in the barbs, resulting in a greater bending curvature for the barbs. Further as shown, regardless of the PA concentration, with increasing curing time, barb curvature decreases and barb thickness increases.

Based on the graph, a predetermined PA concentration may be selected such that the curvature of the barb is within a desired range, for example such as between 0.003 $\mu m^{-1}$ and 0.004 $\mu m^{-1}$. As mentioned above, since a threshold thickness may be necessary for the barbs to exert friction force against skin tissue, a PA concentration may be selected to maximize bending curvature at or above the threshold thickness. For example as shown, for 0.05% w/w PA, a 1.18 s curing time or greater produces barb thickness of at least 100 µm, which corresponds to a bending curvature of approximately 0.003 $\mu m^{-1}$ or lower. For another example, for 0.02% w/w PA, a 1.12 s curing time or greater produces barb thickness of at least 100 µm, which corresponds to a bending curvature of approximately 0.003 $\mu m^{-1}$ or lower. Thus, based on this graph, for a 2% w/w PI concentration, 0.05% w/w PA and 1.18 s curing time may be chosen as the set of fabrication parameters that provide the greatest bending curvature and a threshold barb thickness.

Further, combining the results, since FIG. 8 shows that 3% w/w PI provides the greatest bending curvature for the threshold barb thickness, and FIG. 9 shows that 0.05% w/w PA provides the greatest bending curvature for the same barb thickness at about the same curing time, 3% w/w PI, a 0.05% PA, and 1.2 s curing time may be selected as the optimal fabrication parameters.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the examples should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible examples. Further, the same reference numbers in different drawings can identify the same or similar elements.

The invention claimed is:
1. A microneedle assembly, comprising:
an array of microneedles attached to a base, each of the microneedles comprising a tip and a needle shaft, wherein for at least a plurality of microneedles included in the array of microneedles, each microneedle of the plurality of microneedles comprises:
a plurality of cantilevered barbs protruding outwardly from the needle shaft, wherein the cantilevered barbs of a respective microneedle are arranged in a series of rings along the needle shaft of the respective microneedle, wherein each of the cantilevered barbs of the respective microneedle includes:
a first end that protrudes transversely from the needle shaft of the respective microneedle;
a second end that points towards the base; and
a curved surface between the first end and the second end.

2. The microneedle assembly of claim 1, wherein a length of the at least one cantilevered barb is less than or equal to a radius of a curvature of the curved surface of the cantilevered barb multiplied by $\pi/2$.

3. The microneedle assembly of claim 1, wherein the cantilevered barbs have a triangular profile from a viewpoint above the tip of the microneedle.

4. A microneedle assembly comprising:
a base; and
an array of microneedles attached to the base, each of the microneedles comprising a tip and a needle shaft, wherein, for at least a plurality of microneedles included in the array of microneedles, each microneedle of the plurality of microneedles comprises a plurality of cantilevered barbs, wherein the cantilevered barbs are formed from a polymer material that absorbs liquid to cause the cantilevered barbs to change curvature during absorption of the liquid.

5. The microneedle assembly of claim 1, wherein the plurality of cantilevered barbs comprises:
a first ring of cantilevered barbs protruding outwardly from the needle shaft at a first height from the base; and
a second ring of cantilevered barbs protruding outwardly from the needle shaft at a second height from the base, wherein the second height is different from the first height.

6. A three-dimensionally printed microneedle assembly, comprising:
an array of microneedles formed by exposure of a liquid resin comprised of photopolymers to a light source layer-by-layer through a series of patterns projected onto the liquid resin, wherein, for at least a plurality of the microneedles included in the array, each microneedle of the plurality of microneedles comprises:
a needle shaft; and
a plurality of cantilevered barbs, each of the cantilevered barbs having a first end that protrudes transversely from the needle shaft of the respective microneedle, a second end that points in a downward direction towards a base of the needle shaft, and a curved surface between the first end and the second end that is formed by removal of un-crosslinked monomers from one or more layers comprised of a crosslinking gradient.

7. The three-dimensionally printed microneedle assembly of claim 6, wherein the crosslinking gradient comprises a higher degree of crosslinking at an upper portion of the one or more layers and a lower degree of crosslinking at a bottom portion of the one or more layers.

8. The three-dimensionally printed microneedle assembly of claim 7, wherein the plurality of cantilevered barbs includes:
a first ring of cantilevered barbs protruding outwardly from the needle shaft at a first height from the base; and
a second ring of cantilevered barbs protruding outwardly from the needle shaft at a second height from the base, wherein the second height is different from the first height.

9. A method for fabricating an array of microneedles, comprising:
printing an array of microneedles having a tip and a needle shaft by exposing polymers to a light source layer-by-layer through a series of patterns projected onto a photocurable liquid resin including monomer material, the patterns being horizontal cross sections of the array of microneedles; and
forming one or more cantilevered layers by exposure to the light source for a first predetermined curing time to create initially horizontal, cantilevered barbs extending transversely from the needle shaft from a first end to a second end, wherein the cantilevered barbs have a crosslinking gradient with a higher degree of crosslinking at an upper portion of the cantilevered barbs and a lower degree of crosslinking at a bottom portion of the cantilevered barbs, the cantilevered barbs including at least some un-crosslinked monomers,
rinsing the printed array of microneedles to remove an amount of un-crosslinked monomers from the cantilevered layers, where the removal of un-crosslinked monomers causes shrinkage of the cantilevered layers to induce a curvature to a surface of the cantilevered barbs between the first end and the second end such that the second end points in a downward direction towards a base of the needle shaft, and
post-curing the rinsed array of microneedles to fixate the curvature in the surface of the cantilevered barbs.

10. The method of claim 9, wherein the post-curing comprises drying the rinsed array of microneedles.

11. The method of claim 9, wherein the layers of the microneedles other than the cantilevered layers are exposed to the light source for a second predetermined curing time greater than the first predetermined curing time.

12. The method of claim 9, wherein the array of microneedles are printed on a substrate forming the base for the microneedles.

13. The method of claim 9, wherein each of the cantilevered barbs are formed in a single layer.

14. The method of claim 9, wherein the plurality of cantilevered barbs comprise sets of two or more barbs arranged in two or more rings around the needle shafts of a plurality of the microneedles.

15. The method of claim 9, wherein the first predetermined curing time is selected such that the curvature of the curved surface of the cantilevered barbs is between 0.002 $\mu m^{-1}$ and 0.007 $\mu m^{-1}$.

16. The method of claim 9, wherein the liquid resin includes a photo-initiator and a photo-absorber,
wherein the photo-initiator and the photo-absorber are provided in predetermined concentrations to allow a crosslinking gradient to form in the cantilevered barbs when the polymers are exposed to the light source for the first predetermined curing time.

17. The method of claim 16, wherein the photo-initiator comprises Phenylbis (2,4,6-trimethylbenzoyl) phosphine oxide having a concentration of between 1 and 3% w/w.

18. The method of claim 17, wherein the photo-initiator comprises Phenylbis (2,4,6-trimethylbenzoyl) phosphine oxide having a concentration of 3% w/w.

19. The method of claim 16, wherein the photo-absorber comprises 1-Phenylazo-2-naphthol having a concentration between 0.02 and 0.08% w/w.

20. The method of claim 19, wherein the photo-absorber comprises 1-Phenylazo-2-naphthol with a concentration of 0.05% w/w.

21. The method of claim 16, wherein the predetermined concentration of the photo-absorber is selected such that the curvature of the curved surface of cantilevered barbs is between 0.003 $\mu m^{-1}$ and 0.004 $\mu m^{-1}$.

22. The method of claim 16, wherein the predetermined concentration of the photo-initiator is selected such that the curvature of the curved surface of cantilevered barbs is between 0.003 µm$^{-1}$ and 0.004 µm$^{-1}$.

23. A microneedle assembly formed according to a method comprising the steps of:
   printing an array of microneedles having a tip and a needle shaft by exposing polymers to a light source layer-by-layer through a series of patterns projected onto a photocurable liquid resin including monomer material, the patterns being horizontal cross sections of the array of microneedles; and
   forming one or more cantilevered layers by exposure to the light source for a first predetermined curing time to create initially horizontal, cantilevered barbs extending transversely from the needle shaft from a first end to a second end, wherein the cantilevered barbs have a crosslinking gradient with a higher degree of crosslinking at an upper portion of the cantilevered barbs and a lower degree of crosslinking at a bottom portion of the cantilevered barbs, the cantilevered barbs including at least some un-crosslinked monomers,
   rinsing the printed array of microneedles to remove an amount of un-crosslinked monomers from the cantilevered layers, where the removal of un-crosslinked monomers causes shrinkage of the cantilevered layers to induce a curvature to a surface of the cantilevered barbs between the first end and the second end such that the second end points in a downward direction towards a base of the needle shaft, and
   post-curing the rinsed array of microneedles to fixate the curvature in the surface of the cantilevered barbs.

24. The microneedle assembly of claim 23, wherein the liquid resin includes a photo-initiator and a photo-absorber, and
   wherein the photo-initiator and the photo-absorber are provided in predetermined concentrations to allow a crosslinking gradient to form in the cantilevered barbs when the polymers are exposed to the light source for the first predetermined curing time.

25. The microneedle assembly of claim 1, wherein the curved surface has a curvature between 0.002 µm$^{-1}$ and 0.007 µm$^{-1}$.

26. The microneedle assembly of claim 5, wherein each microneedle of the array of microneedles comprises a respective first ring of cantilevered barbs and a respective second ring of cantilevered barbs.

27. The microneedle assembly of claim 5, wherein each ring of cantilevered barbs includes a predetermined number of non-overlapping cantilevered barbs for which skin adhesion is maximized.

* * * * *